United States Patent [19]

Ekwall et al.

[11] Patent Number: 5,571,164

[45] Date of Patent: Nov. 5, 1996

[54] CARDIAC ELECTRODE DEVICE HAVING AT LEAST A PORTION THEREOF WHICH IS RIBBON SHAPED

[75] Inventors: Christer Ekwall, Spånga; Jakub Hirschberg, Täby; Kurt Högnelid, Bromma, all of Sweden

[73] Assignee: Pacesetter AB, Solna, Sweden

[21] Appl. No.: 533,250

[22] Filed: Sep. 25, 1995

[30] Foreign Application Priority Data

Sep. 29, 1994 [SE] Sweden ................. 9403279

[51] Int. Cl.⁶ ............................................. A61N 1/05
[52] U.S. Cl. ............................................. 607/122
[58] Field of Search .................... 128/642; 607/115, 607/116, 119, 122, 123, 129, 152

[56] References Cited

U.S. PATENT DOCUMENTS

| | | | |
|---|---|---|---|
| 3,876,964 | 4/1975 | Balaster et al. . | |
| 3,911,928 | 10/1975 | Lagergren . | |
| 3,935,864 | 2/1976 | Lagergren | 128/642 |
| 4,399,820 | 8/1983 | Wirtzfeld et al. . | |
| 4,409,994 | 10/1983 | Doring . | |
| 4,506,680 | 3/1985 | Stokes . | |
| 4,573,481 | 3/1986 | Bullara | 128/642 |
| 4,690,148 | 9/1987 | Hoss | 128/639 |
| 4,735,208 | 4/1988 | Wyler et al. | 128/642 |
| 4,903,702 | 2/1990 | Putz | 128/642 |
| 5,005,587 | 4/1991 | Scott | 607/122 |
| 5,052,407 | 10/1991 | Hauser et al. . | |
| 5,092,333 | 3/1992 | Tsuchida et al. | 607/122 |
| 5,329,923 | 7/1994 | Lundquist | 128/642 |
| 5,336,254 | 8/1994 | Brennen et al. | 607/129 |
| 5,466,247 | 11/1995 | Scheiner et al. | 128/642 |

FOREIGN PATENT DOCUMENTS

| | | |
|---|---|---|
| 0009732 | 4/1980 | European Pat. Off. . |
| 0125880 | 11/1984 | European Pat. Off. . |
| 2217993 | 4/1989 | United Kingdom . |

*Primary Examiner*—William E. Kamm
*Assistant Examiner*—George R. Evanisko
*Attorney, Agent, or Firm*—Hill, Steadman & Simpson

[57] ABSTRACT

An electrode device, for intracardiac stimulation and/or defibrillation of heart tissue and/or sensing heart signals in a patient, has a soft, flexible electrode cable with an outer coating of insulation containing at least one elongate conductor connected to an electrode arranged on the electrode cable. In order to attain an electrode device of this kind which is structurally very simple and in which all the electrodes on the electrode cable can be applied to the heart wall in a very simple manner so the entire electrode surface faces the wall and firmly presses against it, the electrode cable is at least partially ribbon-shaped.

19 Claims, 2 Drawing Sheets

CARDIAC ELECTRODE DEVICE HAVING AT LEAST A PORTION THEREOF WHICH IS RIBBON SHAPED

BACKGROUND OF THE INVENTION

1. Find of the Invention

The device relates to an electrode device, for intracardiac stimulation and/or defibrillation of heart tissue and/or sensing heart signals in a patient, of the type having a soft, flexible electrode cable with an outer coating of insulation containing at least one elongate conductor connected to an electrode arranged on the electrode cable.

2. Description of the Prior Art

With the aid of e.g. a bipolar pacemaker electrode device, the heart can be stimulated and its activity sensed with the electrodes arranged on the electrode cable. For good sensing of heart activity and desired stimulation of the heart, it would be very advantageous if the electrodes pressed against the heart wall. Maintaining electrode contact with cardiac tissue is possible with the use of fixing means which, virtually without exception in the art, are arranged only near the electrode located at the distal end of the electrode cable. The other electrodes on the electrode cable are floatingly arranged in the heart.

A fixing means of this kind, which consists of backwardly pointing tines, is known from U.S. Pat. No. 4,409,994. The tines are caused to become embedded in the heart's trabeculae and will accordingly keep the electrode pressed against the heart wall. Tines of this kind, however, could penetrate into heart tissue, thereby damaging the myocardium. Another way to have the electrode press against the heart wall and which is non-traumatic is to use a relatively heavy electrode head, as is described in U.S. Pat. No. 3,911,928. Another electrode device using non-traumatic, a basket-shaped fixing means is known through U.S. Pat. No. 3,935,864. The basket-shaped means, which also serves as the electrode head, ultimately becomes ingrown with tissue and therefore affixed to the wall.

The electrode cable for both these electrodes has a round cross-section. As a result of this shape, the distal electrode head also has a round shape, for the most part, so the arranged conductive surface is usually equally distributed on the electrode head, or the entire surface is conductive. This distribution of the conductive surface is because the cable can rotate on its longitudinal axis. The physician can therefore place the electrode head against the heart wall during implantation, so at least some conductive surface presses against that wall. Since parts of the conductive surface are not in contact with heart wall for stimulation, energy consumption could be needlessly heavy. As a rule, other electrodes arranged on the electrode cable also extend around the electrode cable, leading to the same problem, especially if these electrodes are used for stimulation. As previously noted, the shape of the electrode cable does not generally allow the electrodes arranged behind the distally located electrode to press against the heart wall. The other electrode(s) is/are floatingly arranged in the heart. One example of this is disclosed in the German Patent 3 152 963.

European Application 0 009 732 describes another pacemaker electrode device. In this device, in order for the atrial electrodes to press against surrounding heart wall, one section of the electrode cable is provided with branches forming a basket, these branches being equipped with electrodes. As a result of this construction, such an electrode device is complex and accordingly relatively expensive. It may also be hard to implant.

German Patent 3 912 377 describes a defibrillation electrode device having an elongate electrode cable with a round cross-section which is pre-shaped in such a way that it is helical in the unstretched position, thereby forming a patch-type electrode device. The electrode cable is equipped with a number of adjacent, Outwardly-pointing, wing-like, electrically conductive parts to facilitate the positioning of the defibrillation electrode, in its helical configuration, on the round electrode cable against the external wall of a patient's heart. As a result of these parts, this defibrillation electrode device has a relatively complex structure and is therefore expensive to make.

SUMMARY OF THE INVENTION

An object of the present invention is to provide an electrode device of the above-described type whose structure is very simple and with which all the electrodes on the electrode cable can be made to press against the heart wall in a very simple manner, so that the entire exterior surface of the electrode can face that wall and press firmly against it.

This object is achieved in accordance with the principles of the present invention in an electrode device having an electrode cable which is at least partially ribbon-shaped. This shape gives the electrode cable sufficient torsional strength along the ribbon-shaped sections to prevent the cable from twisting after implantation, and the flat shape is also easy to bend in the cable's longitudinal direction. This means that the experienced implanter can, after the distal end of the electrode cable has been placed in the ventricle, push the electrode cable a little further in, causing the electrode cable to bend, for example, in the atrium and/or the ventricle and pressing its electrodes against surrounding heart wall. It is advantageous if the electrode is ribbon-shaped along its entire length. The ribbon shape gives the cable torsional strength preventing the electrodes from being twisted away from the wall.

According to one embodiment of the invention, the electrode cable is ribbon-shaped in the area in which the electrode is arranged. The electrode cable can also be advantageously ribbon-shaped elsewhere than in the area in which the electrode is arranged. The torsional strength obtained by the electrode cable's ribbon-shape in both of these embodiments is relatively large, so the electrode does not twist out of the desired position after implantation.

In another embodiment of the invention, the conductor has a wavy shape in the ribbon-shaped part of the electrode cable. The electrode cable can then be stretched without damaging the conductor.

In a further embodiment, in which the electrode cable is equipped with at least two conductors, the conductors are braided, at least in the ribbon-shaped part of the electrode cable. In this manner, the torsional strength of the electrode cable can be further enhanced.

According to the invention, the electrode can be arranged on one side of the ribbon-shaped part of the electrode cable. This would ensure that the entire electrode surface faces in the desired direction and presses against heart wall.

In another embodiment of the invention, at least one longitudinal side of the ribbon-shaped part of the electrode cable has an irregular shape, e.g. a zig-zag-shape, preferably along a section in the electrode area. During implantation, the irregularly shaped longitudinal side would become entangled in the heart's trabeculae and then serve as a fixation means.

The ribbon-shaped part of the electrode cable can also be advantageously provided with holes and/or pits, preferably in the electrode area. Tissue would grow into the holes or pits of this embodiment after the implantation, thereby achieving good fixation of the electrode cable.

In one advantageous embodiment of the invention, the electrode cable is equipped along the ribbon-shaped sections with channels, preferably arranged along the electrode cable's longitudinal sides, with wires, running in the these channels, which are attached to the distal end of the electrode cable and which extend beyond the proximal end of the electrode cable. When one of the wires is pulled, or two are pulled simultaneously, the electrode cable can be maneuvered longitudinally and laterally.

DESCRIPTION OF THE PREFERRED EMBODIMENTS

Figure 1:
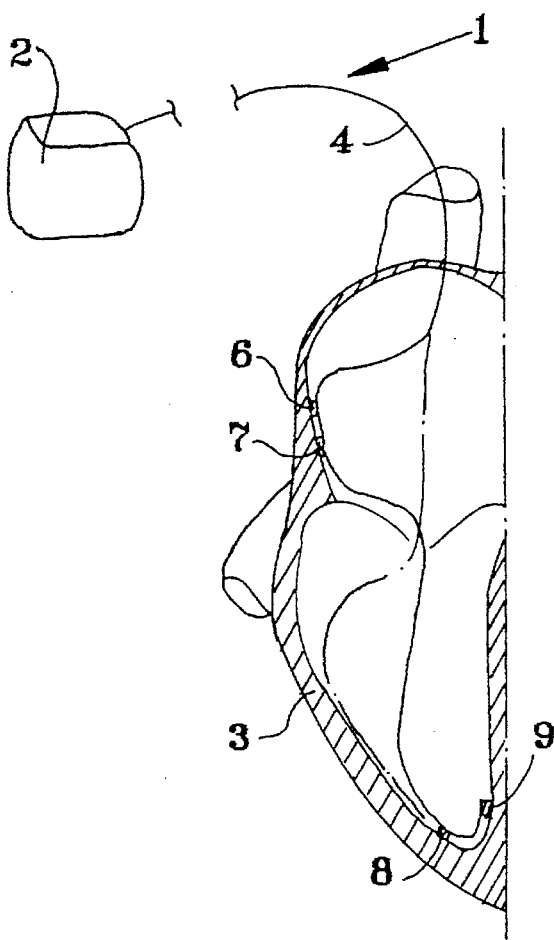
FIG. 1 is a section through a heart with an electrode device implanted therein constructed according to the principles of the present invention.

FIG. 1 shows a pacemaker electrode device 1 connected to a pacemaker 2 and applied in a patient's heart 3. The electrode device has a soft, flexible electrode cable 4 which, in this embodiment, is ribbon-shaped along its entire length. The electrode cable 4 is provided with an external layer of insulation 5, and conductors (described below), running from the electrode proximal end of the cable 4 and connected to separate electrodes arranged on the electrode cable 4, are embedded in the layer of insulation in this embodiment, the electrode device 1 is equipped with four electrodes 6, 7, 8 and 9, two of which, electrodes 6 and 7, being placed in such a way that they are arrayed in the atrium after the electrode device has been implanted. The other two electrodes 8 and 9 are arranged at the distal end of the electrode cable 4 and are placed in the ventricle.

Figure 2:
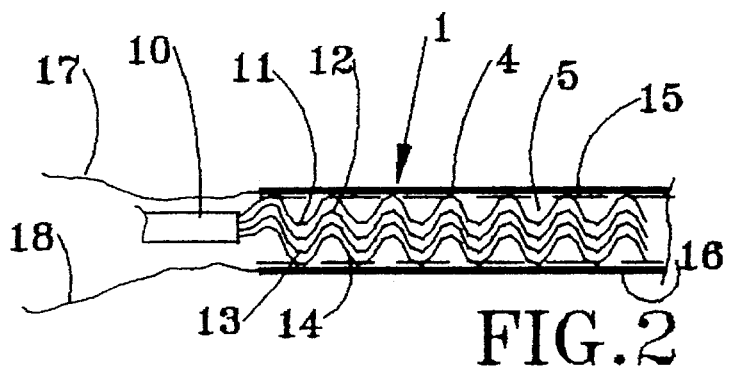
FIGS. 2–10 respectively illustrate a portion of an electrode device of the invention in different embodiments.

In FIG. 2 the proximal end of the electrode device 1 is shown with the electrode cable 4 and a pin 10 which is connectable to the pacemaker 2. The conductors 11–14 are shown in FIG. 2, even though they are actually embedded in the layer of insulation 5. The conductors 11–14, which are insulated from each other, run parallel to each other and are arranged in a wavy shape in the ribbon-shaped electrode cable 4. This ensures that the conductors only assume a less wavy configuration, i.e., a configuration with larger peak-to-peak distances between the "waves," when the electrode cable 4 is stretched in its longitudinal direction, thereby preventing broken conductors.

Figure 3:
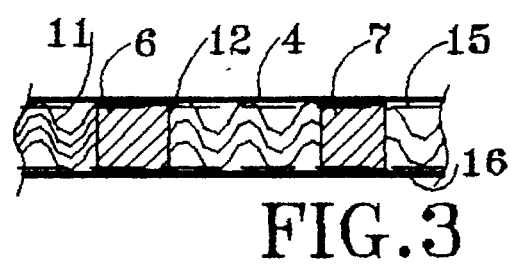
Figure 4:
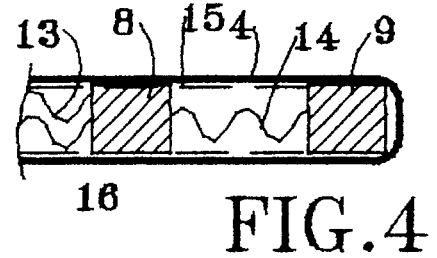

FIGS. 3 and 4 show that each conductor 11–14 is connected to a separate electrode, the conductor 11 being connected to electrode 6, the conductor 12 to electrode 7, the conductor 13 to electrode 8 and the conductor 14 to the distal electrode 9.

The electrode device 1 and its electrode cable 4 can be implanted with the cable 4 being introduced into the heart 3 via a vein using a known (and therefore not shown) catheter into which the electrode cable 4 is inserted. The catheter is removed after the electrode cable 4 has been introduced into the heart 3. In order to control the movements of an implanted electrode cable 4 in the heart 3, the electrode cable is equipped with channels 15 and 16, preferably arranged along the longitudinal sides of the electrode cable 4. Wires 17 and 18 running in the respective channels 15 and 16 are connected to the distal end of the electrode cable 4 and extend beyond the proximal end of the electrode cable 4, as shown in FIG. 2. When one of the wires 17 or 18 is pulled, or both are pulled simultaneously while the electrode cable 4 is kept from moving, the electrode cable 4 can be maneuvered laterally but especially longitudinally, causing the electrode cable to bend and assume a shape such as the shape shown in FIG. 1. Since the electrode cable 4 is ribbon-shaped, the cable can assume a curved shape in which it presses against the heart wall, and because the electrode cable 4 resists twisting, the entire surface of all of the electrodes 6–9, if arranged on one side of the ribbon-shaped electrode cable 4, will press against the heart wall, even in the atrium. In the extended position, the wires 17 and 18 can be affixed to the proximal end so the electrode cable remains in the described position. The operator can also make the electrode cable 4 assume other shapes. An example of one such shape is shown with the dot-and-dash line in FIG. 1, the described electrodes 6–9 being arranged at some other suitable location on the electrode cable 4.

If the electrode device is intended for defibrillation of the heart, the defibrillation electrode is preferably arranged on the side of the ribbon-shaped electrode cable 4 facing away from the heart wall in order to prevent burn damage.

Figure 5:
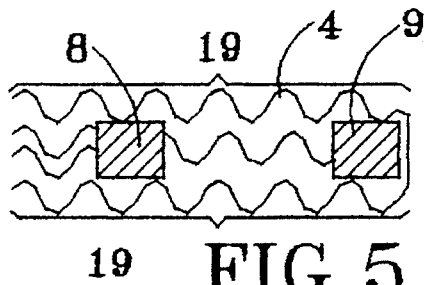
Figure 6:
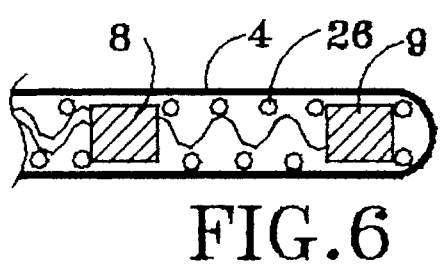

FIG. 5 shows the distal end of a ribbon-shaped electrode cable 4 according to an embodiment of the invention. This electrode cable 4 differs from the above-described embodiment by having irregularly shaped, e.g. zig-zag-shaped, longitudinal sides 19. These irregularly shaped longitudinal sides 19 are preferably arranged along a section in the area for the electrodes 8 and 9 and serve as a fixing means for making contact with the heart's trabeculae. The electrode cable 4 can also be provided with irregularly shaped longitudinal sides along other sections of the electrode cable 4, preferably along a section in the area for some other electrode than the above-mentioned electrodes. The ribbon-shaped electrode cable 4 can also be provided with holes and/or depressions 26, preferably in the area for the electrodes 8 and 9, as shown in FIG. 6. After heart tissue grows into them, these holes and/or depressions 26 serve to affix the electrode cable 4. In order to further ensure good fixing of the ribbon-shaped electrode cable 4, a combination of irregularly shaped longitudinal sides 19 and holes and/or depressions 26 is also possible.

Figure 7:
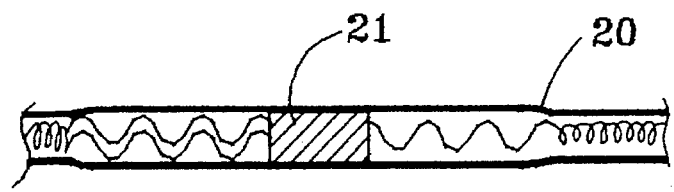

FIG. 7 shows another embodiment of an electrode cable 20 according to the invention which is ribbon-shaped only in a section (of which there may be several) in which an electrode 21 is arranged. This electrode cable 20 can have a conventional, round cross-section with helical conductors, whereas conductors in the ribbon-shaped section can be wavy.

Figure 8:
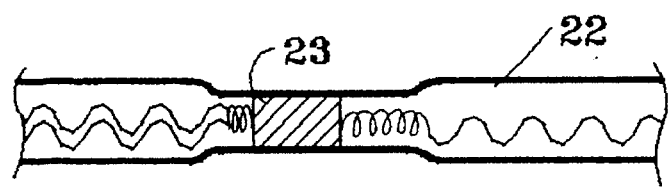

FIG. 8 shows a further embodiment of an electrode cable 22 according to the invention which is ribbon-shaped elsewhere than in the section in which the electrodes are arranged. only one electrode 23, ring-shaped in this embodiment, is shown in the FIG. 8. This ring shape can be replaced with a conductive surface facing the heart after the electrode has been implanted.

Figure 9:
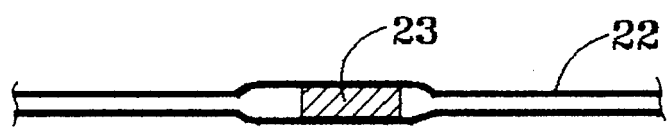

FIG. 9 shows a lateral view of the electrode cable 22 which clearly shows that parts of the electrode are ribbon-shaped.

Within the scope of the invention, an electrode cable (not shown here) can be devised so the cable's distal end with the electrodes has a round cross-sectional configuration, and the electrode cable is ribbon-shaped along each section in which an electrode is arranged.

Figure 10:
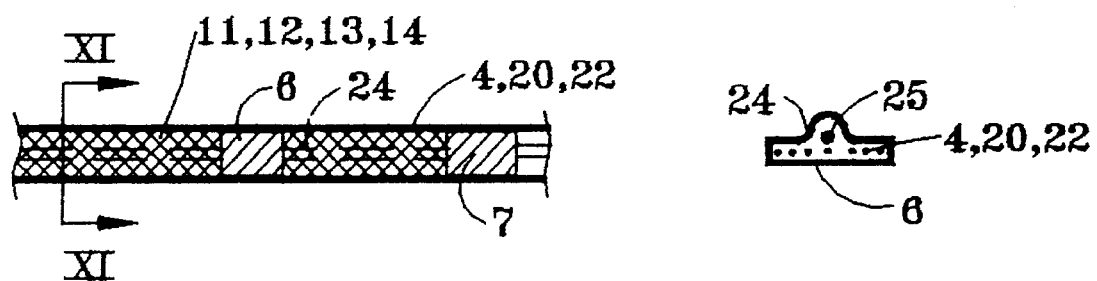

FIG. 10 shows that the conductors 11–14 for electrodes, e.g. 6 and 7, in the ribbon-shaped part of any of the electrode cables 4, 20 or 22, can be braided. In this embodiment, the conductors, each connected to a separate electrode, are naturally insulated against each other. The advantage of this embodiment is that the design increases the electrode cable's torsional strength.

Figure 11:
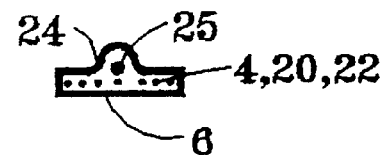
FIG. 11 is a cross-section through an electrode cable according to FIG. 10 taken along line XI—XI.

FIG. 11 is a sectional view showing that any of the electrodes cable 4, 20 or 22 in FIG. 11 can be provided with a bead 24, running along the entire length of the electrode cable 4, 20 or 22, with a through channel 25 for a stylet. The introductory catheter mentioned in conjunction with FIG. 1 would be unnecessary in this embodiment.

The electrode cables 20 and 22 described in conjunction with FIGS. 7–9 can be equipped with channels, arranged along the longitudinal sides of the ribbon-shaped sections, holding wires attached at the distal end of the electrode cables 20 and 22 and extending beyond the proximal end of the electrode cables 20 and 22. These electrode cables 20 and 22 can accordingly be maneuvered in the same way as was described in conjunction with FIGS. 1–4.

With an at least partial band shape, the electrode cable acquires torsional strength ensuring that the electrode always assumes a stable position after implantation. Moreover, the electrode cable can be devised in such a way that electrodes arranged behind the distal electrodes, e.g. in the atrium, can press against heart wall with the electrode facing toward or away from the wall.

Although modifications and changes may be suggested by those skilled in the art, it is the intention of the inventors to embody within the patent warranted hereon all changes and modifications as reasonably and properly come within the scope of their contribution to the art.

We claim as our invention:

1. An electrode device for in vivo delivery of electrical signals to and reception of electrical signals from cardiac tissue in a heart having a heart wall, said electrode device comprising:

at least one elongate electrical conductor;

a flexible electrode cable having an outer coating of electrical insulation and containing said at least one elongate conductor, said flexible electrode cable having at least a portion which is ribbon-shaped;

an electrode, having a substantially flat exposed electrode surface, carried on said electrode cable and electrically connected to said elongate conductor, said portion of said cable which is ribbon-shaped forming means for endocardially retaining said exposed electrode surface in substantially flat contact with said heart wall; and means for endocardially affixing said electrode cable to said heart wall.

2. An electrode device as claimed in claim 1 wherein said electrode cable is ribbon-shaped along an entirety of its length.

3. An electrode device as claimed in claim 1 wherein said electrode cable is ribbon-shaped only in a section of said electrode cable at which said electrode is disposed.

4. An electrode device as claimed in claim 1 wherein said electrode cable is ribbon-shaped at a portion thereof other than a section at which said electrode is disposed.

5. An electrode device as claimed in claim 1 wherein said elongate conductor has a wavy shape and wherein said elongate conductor is disposed in a portion of said electrode cable which is ribbon-shaped.

6. An electrode cable as claimed in claim 1 comprising at least two elongate conductors, said at least two elongate conductors being braided, and said at least two elongate conductors being braided at least in a part of said electrode cable which is ribbon-shaped.

7. An electrode device as claimed in claim 1 comprising a plurality of elongate conductors and a plurality of electrodes, each elongate conductor respectively connected to one of said electrodes, and each elongate conductor being individually electrically insulated.

8. An electrode device as claimed in claim 1 wherein said electrode is disposed at one side of said ribbon-shaped portion of said electrode cable.

9. An electrode device as claimed in claim 1 wherein said cable has a longitudinal direction along which said elongated conductor has a maximum extent and wherein said ribbon-shaped portion of said electrode cable has at least one irregularly shaped longitudinal side extending in said longitudinal direction.

10. An electrode device as claimed in claim 9 wherein said at least one irregularly shaped longitudinal side has a zig-zag shape.

11. An electrode device as claimed in claim 9 wherein said ribbon-shaped portion of said electrode cable having said at least one irregularly shaped longitudinal side is disposed in a section of said electrode cable in which said electrode is disposed.

12. An electrode device as claimed in claim 1 wherein said means for affixing comprise plurality of holes in said ribbon-shaped portion of said electrode cable.

13. An electrode device as claimed in claim 12 wherein said holes in said ribbon-shaped portion of said electrode cable are disposed in a section in which said electrode is disposed.

14. An electrode device as claimed in claim 1 wherein said ribbon-shaped portion of said electrode cable has a plurality of depressions therein.

15. An electrode device as claimed in claim 14 wherein said depressions in said ribbon-shaped portion of said electrode cable are disposed in a section in which said electrode is disposed.

16. An electrode device as claimed in claim 1 wherein said electrode cable has a channel therein extending along a complete length of said electrode cable, adapted to receive a stylet.

17. An electrode device as claimed in claim 1 wherein said electrode cable has a longitudinal axis, and wherein said at least one ribbon-shaped portion has a plurality of channels therein extending substantially parallel to said longitudinal axis, and aid electrode device further comprising a plurality of wires respectively disposed in said channels and extending between opposite ends of said electrode cable for adjusting a position of said electrode cable during implantation thereof.

18. An electrode device as claimed in claim 17 wherein said cable has a longitudinal direction along which said elongated conductor has a maximum extent and wherein said at least one ribbon-shaped portion of said electrode has longitudinal sides extending in said longitudinal direction, and wherein said channels are disposed at said longitudinal sides.

19. An electrode device for in vivo delivery of electrical signals to and reception of electrical signals from cardiac tissue, said electrode device comprising:

at least one elongate electrical conductor;

a flexible electrode cable having an outer coating of electrical insulation and containing said at least one elongate conductor, said flexible electrode cable being at least partially ribbon-shaped;

an exposed electrode carried on said electrode cable and electrically connected to said elongate conductor; and said cable having a longitudinal direction along which said elongated conductor has a maximum extent, and said ribbon-shaped portion of said electrode cable having at least one zig-zag shaped longitudinal side extending in said longitudinal direction.

* * * * *